United States Patent [19]
Choi et al.

[11] Patent Number: 5,089,517
[45] Date of Patent: Feb. 18, 1992

[54] NEUROPROTECTION BY INDOLACTAM V AND DERIVATIVES THEREOF

[75] Inventors: Dennis W. Choi; Dean M. Hartley, both of Stanford, Calif.

[73] Assignee: The Board of Trustees of the Leland Stanford Junior University, Stanford, Calif.

[21] Appl. No.: 562,680

[22] Filed: Aug. 3, 1990

[51] Int. Cl.$^5$ .................. A01N 43/90; C07D 487/02
[52] U.S. Cl. .................. 514/411; 540/461; 548/433
[58] Field of Search .................. 514/411, 465, 466; 540/460, 461, 451; 548/433

[56] References Cited

PUBLICATIONS

Nakatsuka et al. Tetrahedran Lett. (1987) 28: 2265-2268.
Maritaki et al. Tetrahedron Lett. (1988) 29: 6267-6270.
Okabe et al. Chem. Pharm. Bull. (1989) 37: 563-564.
Rothman, S., "Synaptic Release of Excitatory Amino Acid Neurotransmitter Mediates Anoxic Neuronal Death", J. Neurosci. (1984) 4:1884-1891).
Simon, R. P. et al., "Blockade of N-Methyl-B-Aspartate Receptors May Protect Against Ischemic Damage in the Brain", Science (1984) 226:850-852).
Weiloch, T., "Hypoglycemia-Induced Neuronal Damage Prevented by an N-Methyl-D-Aspartate Antagonist", Science (1985) 230:681-683.
Choi, D., "Glutamate Neurotoxicity and Diseases of the Nervous System" Neuron (1988) 1:623-634.
Harata et al., Bull. Chem. Soc. Japan (1966) 39:1773-1775.
Irie et al., Int. J. Cancer (1985) 36:485-488.
Fujiki et al., Proc. Japan Acad., Ser. D, (1985) 61:45-47.
Horiuchi et al., Gann. (1984) 75:837-840.
Irie and Coshimizu, Mem. Coll. Agric., Kyoto Univ., (1988) 132:1-59.
Jan. 1990 New Products Bulletin of L. C. Services Corporation, Woburn, Mass.

Primary Examiner—Glennon H. Hollrah
Assistant Examiner—Brian M. Burn
Attorney, Agent, or Firm—Cooley Godward Castro Huddleson & Tatum

[57] ABSTRACT

A method for reducing adverse effects of neurotoxic injury, which comprises administering to a patient susceptible to neurotoxic injury an effective amount, sufficient to reduce the injury, of a compound having an indolactam V ring system. Particularly preferred are compounds having ring stereochemistry as indicated in the following formula:

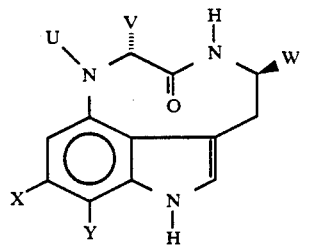

The indicated substituents show preferred locations of substituents; preferred substituents are defined in the specification.

18 Claims, No Drawings

NEUROPROTECTION BY INDOLACTAM V AND DERIVATIVES THEREOF

INTRODUCTION

1. Technical Field

The present invention is in the field of pharmacology and specifically relates to a new use of indolactams to protect central neurons from neurotoxic injury.

2. Background

The central nervous system (CNS) is exquisitely sensitive to brief hypoxia, while other tissues may survive during hypoxia for extended periods. Recently, attention has been focused on a possible role of the excitatory neurotransmitter glutamate, and related compounds, in the pathogenesis of the neuronal injury produced by a variety of CNS insults, including hypoxia. Glutamate both is present at high concentrations in the mammalian CNS and is toxic to central neurons (glutamate is known to be a broad-spectrum agonist with efficacy at three subtypes of excitatory amino acid receptors—kainate, α-amino-3-hydroxy-5-methyl-4-isoxazolepropionic acid (AMPA) and N-methyl-D-aspartate (NMDA)). Evidence for a role of glutamate in mediating hypoxic neuronal injury is shown by the fact that certain glutamate antagonists can attenuate the acute neuronal injury produced by hypoxia, ischemia, and hypoglycemia. These pathological conditions are thought to induce a toxic buildup of glutamate in the extracellular space, leading to overstimulation of glutamate receptors, as demonstrated by a number of recent studies.

The observed protective effects of glutamate antagonists on central neurons have raised the possibility that such drugs might have clinical therapeutic utility in hypoxic CNS injury. However, the drugs previously known are not currently available from a clinical standpoint (e.g., have not completed clinical trials), and little is known of their effects in man.

In the process of investigating various compounds for their ability to reduce the adverse effects of neurotoxic injury, one of the present inventors previously discovered that classical morphine-like opioids and their inactive enantiomers are useful in preventing or reducing the adverse effects of neurotoxic injury caused by release of glutamate from cells. Preferred compounds were determined to be dextrorotatory enantiomers of morphine-like opiates (especially morphinans) having a ring structure in which the 3-dimensional arrangement of the rings is a mirror image of the ring arrangement in morphine. These discoveries were described in U.S. patent application Ser. No. 934,733, filed Nov. 25, 1986, now U.S. Pat. No. 4,806,543.

Although this prior discovery is extremely useful in bringing into existence a new treatment for neurotoxic injury, the dextrorotatory enantiomers of opioids of the prior invention were most useful against only one of the three types of excitatory amino acid receptors previously mentioned, namely the NMDA receptor. The neurotoxic injury caused by toxic overstimulation of the other receptor types, namely kainate and AMPA, was not affected by opioids or opioid enantiomers.

Accordingly, there remains a need for new techniques and compositions capable of reducing neurotoxic injury resulting from toxic effects mediated at all three types of excitatory amino acid receptors.

Several different compounds having an indole nucleus with a 9-membered lactam ring between the 3 and 4 positions are known. These include compounds of the class known as teleocidins and the seaweed toxin lyngbyatoxin A.

The common structural elements of the teleocidins and related compounds has been named (−)-indolactam V and has the structure set forth below:

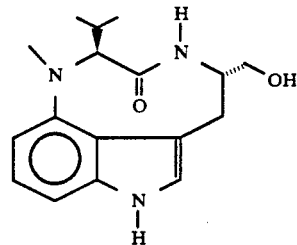

Here and elsewhere in this specification, conventional designations of stereochemistry are used; i.e., a bond extending upward toward the viewer from the plane of the page is represented by ▬, a bond extending behind the page is represented by ////, a bond that is in the plane of the page or that is not part of a chiral center is represented by ___ °, and a bond in a formula that represents both possible orientations of the chiral center is shown by ∼∼.

Indolactam compounds having the (−)-indolactam V ring system, like phorbol esters, can activate the cellular enzyme protein kinase C (PKC). These indolactam compounds also share a number of biological activities with phorbol esters, including skin inflammatory effects and tumor promotion.

RELEVANT LITERATURE

Various investigators have studied the relationship of glutamate antagonists to hypoxia (Rothman, S., "Synaptic Release of Excitatory Amino Acid Neurotransmitter Mediates Anoxic Neuronal Death", *J. Neurosci.* (1984) 4:1884–1891), ischemia (Simon, R.P., et al., "Blockade of N-methyl-B-aspartate Receptors May Protect Against Ischemic Damage in the Brain", *Science* (1984) 226:850–852), and hypoglycemia (Weiloch, T., "Hypoglycemia-Induced Neuronal Damage Prevented by an N-methyl-D-aspartate Antagonist", *Science* (1985) 230:681–683). The possible participation of glutamate receptor-mediated toxicity in the neuronal death associated with these and other diseases, including Huntington's disease, Alzheimer's disease, and amyotrophic lateral sclerosis, has been recently reviewed (Choi, D., "Glutamate neurotoxicity and diseases of the nervous system" *Neuron* (1988) 1:623–634). The structure of dihydroteleocidin B monobromoacetate is described in Harata et al., *Bull. Chem. Soc. Japan* (1966) 39:1773–1775. A number of different structure-activity studies of teleocidins have been published; see, for example, Irie et al., *Int. J. Cancer* (1985) 36:485–488; Fujiki et al., *Proc. Japan Acad.*, Ser. D, (1985) 61:45–47; Horiuchi et al., *Gann.* (1984) 75:837–840; and Irie and Coshimizu, *Mem. Coll. Agric.*, Kyoto Univ., (1988) 132:1–59. Additionally, see the January 1990 New Products Bulletin of L.C. Services Corporation, Woburn, Mass., U.S.A., which describes (−)-7-octylindolactam V. This last publication includes a review of recent indolactam chemistry and provides a series of 38 publications in the indolactam field including a number of structure-activity studies.

SUMMARY OF THE INVENTION

The present invention provides a method for reducing the adverse effects of neurotoxic injury by administering to a patient susceptible to neurotoxic injury an amount, sufficient to reduce neurotoxic effects caused by glutamate or other excitatory amino acids, of a compound having an indolactam V ring system, particularly compounds in which the ring system is a mirror image enantiomer of the indolactam V compounds that are known to have tumor promoting properties. While compounds having both the natural stereochemistry and the mirror-image enantiomeric stereochemistry are active for the purpose of the present invention, those compounds that have the mirror-image stereochemistry do not appear to have tumor promoting properties and are therefore preferred. The preferred stereochemistry is referred to as the (+)-indolactam V ring system in contrast to the naturally occurring (−)-indolactam V ring system. The preferred stereochemistry is shown in the formula below:

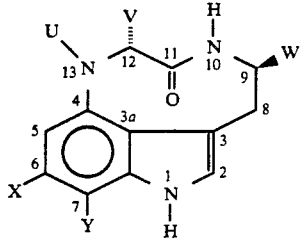

The numbering system used throughout the specification is shown in the ring system above. Various substituents can be present on the ring system without adversely affecting the practice of the present invention. Preferred locations of substituents are shown by U, V, W, X, and Y in the formula above. Particularly preferred are hydrophobic substituents at the 6, 7, or both 6 and 7 positions, which are the positions bearing hydrophobic substituents in the teleocidin series, although substitution at other positions is also possible. Specific examples and additional detail on the substituent patterns that can be used in the practice of the present invention are set forth below in the description of specific embodiments.

DESCRIPTION OF SPECIFIC EMBODIMENTS

The present invention has arisen out of findings that compounds with the indolactam V ring system have substantial ability to protect central neurons against toxic injury. For example, indolactam V compounds have been shown to prevent destruction of neocortical neurons induced by exposure to various glutamate agonists, such as kainate, NMDA, and AMPA.

There has been considerable interest in the past in compounds having the (−)-indolactam V ring structure because of the phorbol ester-like activity of such compounds. In addition to the naturally occurring teleocidins, a number of synthetic analogs, such as 7-octylindolactam V, have been prepared. Both the phorbol esters and the teleocidins and their derivatives have a number of interesting physiological properties, such as giving rise to tissue inflammation, inducing mouse skin ornithine decarboxylase, aggregating certain human lymphoblastoid cells, promoting tumors, inhibiting phorbol ester receptor binding, and stimulating DNA synthesis in many cell types. Many of these activities are adverse and are detrimental to the use of (−)-indolactam V compounds for pharmacological purposes. However, as the present invention is intended to prevent death and other adverse effects to central neurons during toxic injury situations, the side effects can be considered relatively minor when compared to the possibility of brain damage. Accordingly, even the more toxic (−)-indolactam V compounds of the invention can find use under severe toxic conditions.

However, it has been discovered that the stereochemistry of the ring system does not need to be retained in order for neuroprotective activity to be retained. (+)-Indolactam V ring systems are equally effective or in some cases more effective than their phorbol ester-like counterparts.

The ring system itself has no asymmetric centers in the absence of substituents on the ring. There are two asymmetric carbon atoms in the indolactam V ring system as found in most naturally indolactams that function as isomeric centers. These are the carbon atoms at positions 9 and 12. Accordingly, there are four possible stereoisomers of the basic indolactam V ring system as it is most typically found. Additional isomers of these molecules can occur as a result of the existence of stereochemical centers in various substituents present on the basic ring system. None of these stereochemical centers appear to have an essential configuration that is required for neuroprotective activity.

Although any of the four basic isomers can be used in the practice of the invention, it is likely that the compounds most readily available for use (i.e., by purchase from commercial sources) will be the (−)-indolactam V compounds and their enantiomers, the (+)-indolactam V compounds, as these are the targets of previous synthetic efforts. As is known in the art, the relationship of enantiomers to each other is that of an object and its mirror image. Because of the three-dimensional nature of a binding reaction of a compound and its receptor, the enantiomer of a compound having biological activity is often inactive because it cannot bind with the receptor of the active molecule. However, the present invention, as previously indicated, is not limited to a particular enantiomer.

Enantiomers are traditionally referred to by their ability to rotate polarized light as either being dextrorotatory or levorotatory. However, although compounds with similar stereochemistry typically rotate light in the same direction, it is possible that the substitution of one functional group for another without changing, as in this case, the basic ring structure stereochemistry will result in a different rotation of light. Accordingly, in the present application preferred compounds of the invention are defined as their having a ring system with the same stereochemistry as (+)-indolactam V, since this definition is more precise than by referring to the physical ability of such molecules to rotate polarized light in a particular direction. Nevertheless, compounds having a ring structure with the stereochemistry of teleocidins are typically levorotatory as a whole. Accordingly, dextrorotatory indolactam V derivatives typically represent preferred compounds for use in the method of the present invention. It will be realized, however, that related compounds (which may have either ring structure) may rotate polarized light either in a dextrorotatory or levorotatory fashion depending on particular substituents that are present.

The major advantage of dextrorotatory indolactam V compounds over conventional levorotatory compounds is twofold: (1) greater anti-neurotoxic potency and (2) virtual absence of phorbol ester-like activity. This advantage allows high dose levels of compounds of the invention to be used without complicating side effects.

Compounds of the invention that can be utilized to protect against neurotoxic injuries include indolactam V itself and derivatives thereof having the same tricyclic ring system. Substituents on the ring system are typically hydrogen, hydrocarbon groups, and hydrocarbon groups substituted with one or more substituents selected from the group consisting of halogen, carbonyl, alkoxy, alkyl amino, and dialkyl amino, with the proviso that no substituent on the indolactam ring system other than a hydroxymethyl substituent at the 9 position (which is present in some but not necessarily all compounds) will render the total molecule more hydrophilic than the same compound with a hydrogen in place of that substituent. Hydrophilicity can readily be determined by measuring the partition coefficient of compounds of the invention between diethyl ether and water. In a typical measurement of partition coefficient, an ether solution is made 0.05M in the compound in question and equilibrated with an equal volume of water. Measurement of the concentration of the compound of interest in either the ether or the water solution allows determination of the partition coefficient using standard calculations.

Certain substituents are particularly preferred at specific locations on the indolactam V ring system. A number of preferred substituents and ring locations are shown in the following formula:

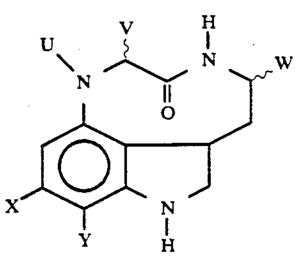

wherein U is H or methyl; V is H or an alkyl group; W is H, an alkyl group, or an alkyl group substituted with a hydroxyl group; and X and Y independently represent hydrogen or a hydrophobic substituent containing up to 15 carbon atoms. Hydrophobic substituents are generally hydrocarbon groups or hydrocarbon groups substituted with one or more heteroatom substituents (e.g., halogen, oxygen, nitrogen, or sulfur in the form of typical organic substituents, such as those containing hydroxyl, carbonyl, amino, ether, ester, amido, carboxyl, thioether, thioester, mercapto, and other simple organic functional groups as well as various cyclic substituents including heteroatoms, especially oxygen and nitrogen). Hydrocarbon groups include alkyl, alkenyl, and alkynyl groups and further include linear, branched, and cyclic (saturated, unsaturated, and aromatic) hydrocarbon groups. Substituents at positions other than the 6 and 7 positions of the ring preferably contain 5 carbon atoms or fewer. Substituents at the 6 and 7 positions are often larger, containing up to 20 carbon atoms in preferred compounds, more typically 15 or fewer, even more typically 10 or fewer.

In particular, compounds in which U is methyl, V is an isopropyl group, and W is a hydroxymethyl group are preferred. When U, V, and W represent these groups and X and Y represent hydrogen, the resulting compound is indolactam V itself. Derivatives of indolactam V having X and Y substituents as described herein are also preferred.

In particular, one group of compounds that is preferred is the group of indolactam V compounds of the general formula above in which X represents hydrogen and Y represents a hydrophobic substituent containing up to 15 carbon atoms. In particular, Y can represent a hydrocarbon group having an isoprenoid structure. Teleocidins typically have this type of preferred structure. Another preferred group of compounds includes derivatives of indolactam V in which X and Y together represent a cyclic hydrocarbon group when taken together with the ring carbons at positions 6 and 7. The cyclic hydrocarbon formed by the indicated groups is typically a 6-membered ring. The total number of carbon atoms in the combined X-Y substituent is typically 20 or fewer, more typically 15 or fewer.

A number of relatively simple derivatives of indolactam V exist in which a simple hydrocarbon structure is present as the Y substituent. For example, 7-octylindolactam V has been synthesized in both dextrorotatory and levorotatory forms. Other compounds having an alkyl substituent in the Y position, typically a linear alkyl group, are also preferred.

As a guide to nomenclature and for the purposes of identifying compounds within the scope of the invention, the Chemical Abstracts Service uses the following systematic name for (−)-indolactam V: (2S-(2R*,5R*))-1,2,4,5, 6,8-hexahydro-5-hydroxymethyl)-l-methyl-2-(1-methylethyl)-3H-pyrrolo(4, 3,2,-gh)-4,4-benzodiazonin-3-one. The 2S designation represents absolute stereochemistry at atom C2 of the ring system. The 2R* and 5R* derive from CAS nomenclature rules designating configurations of stereocenters determined relative to each other. Thus, the absolute configuration of C5 is S rather than R.

Because systematic names are cumbersome, they are typically not used among biomedical scientists. Most names used in the biomedical community use the indolactam V structure as a beginning point and name compounds as derivatives of this basic structure. Additionally, a number of non-systematic nomenclature systems exist, particularly for natural products such as the teleocidins. A number of exemplary teleocidins and their structures are shown below:

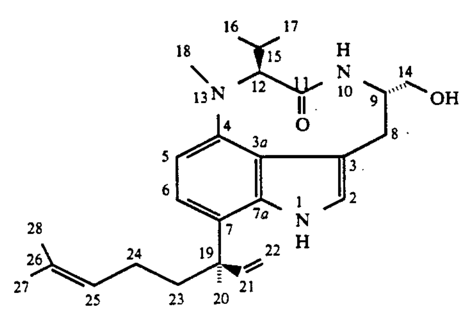

Teleocidin A-1

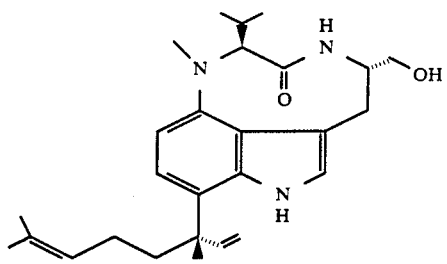

Teleocidin A-2

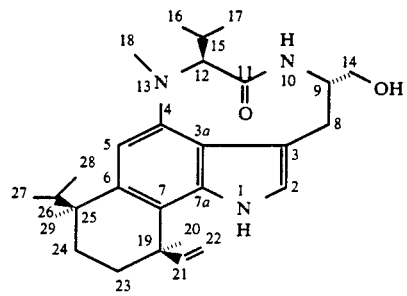

Teleocidin B-1

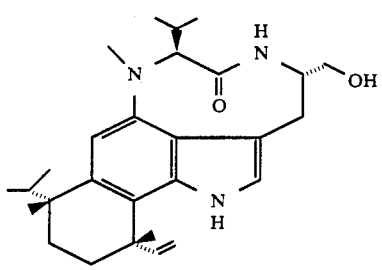

Teleocidin B-2

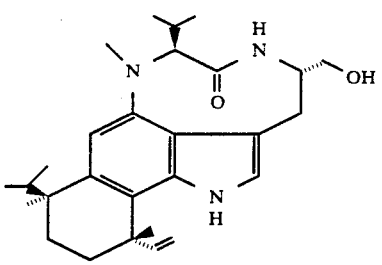

Teleocidin B-3

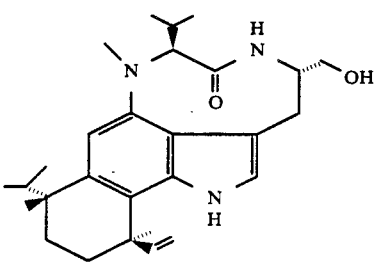

Teleocidin B-4
(Olivoretin D)

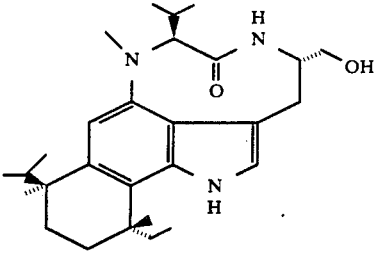

Dihydroteleocidin B-3

It should be recognized that these compounds are illustrative of the invention and that other compounds having the basic structure as described herein are also expected to have the indicated activity. Whether any specific, newly investigated indolactam will have the desired protective activity can readily be determined by test procedures described in detail in the examples below. Compounds capable of protecting central neurons against glutamate toxicity can be selected by forming a reaction test composition containing central neurons and sufficient glutamate, or other glutamate receptor agonist, to induce toxic injury to the neurons, adding a compound containing a indolactam ring system to the test composition, and comparing neurotoxic injury to the neurons in the presence of the compound to neurotoxic injury in the test composition in the absence of the test compound. The test composition contains nutrients capable of sustaining the life of the cells in the absence of glutamate (or its equivalent); a number of useful cell culture media are commercially available. Either quantitative or qualitative evaluation of the cells can be made after addition of an excitatory amino acid, especially glutamate, to the culture medium. For example, the culture medium can be analyzed for release of components from the cells (e.g., enzymes that are normally retained in the cellular cytoplasm) as a measure of damage to the neurons, thereby providing a quantitative evaluation.

The compounds of the invention can be utilized to protect against a number of neurotoxic injuries caused by the action of excess glutamate or related compounds on central neurons. There is a considerable body of evidence indicating that the neurotoxicity of the endogenous excitatory amino acid glutamate (and/or related endogenous compounds, including quinolinate, homocysteate, and aspartate) play a critical role in the pathogenesis of central neuronal (brain, brain stem, spinal cord, or retinal) injury in the setting of several acute and chronic neurological diseases, including ischemia, hypoxia, hypoglycemia, epilepsy, infection, trauma, Huntington's disease, amyotrophic lateral sclerosis, Parkinson's disease, and Alzheimer's disease. See the discussion of relevant literature in the Background section of this specification for a number of scientific publications describing the relationship of excitatory amino acids to neurotoxic injury.

Glutamate is typically released from cells when insufficient energy is available for the cells to maintain their normally high internal glutamate concentrations. High internal glutamate concentrations are maintained by an active transport system that utilizes energy. Under low energy conditions, such as during ischemia, hypoxia, or hypoglycemia, glutamate is released by the cells. Release of glutamate stimulates further release of glutamate, resulting in a cascade of neurotoxic damage.

Experimental work in the laboratory of the inventor has established a cortical cell culture model system capable of accessing central neuronal cell injury. Using this system, it has been demonstrated that glutamate is a much more potent neurotoxin than previously believed. Additional experimental evidence in the inventor's laboratory has indicated that blockade of only one of the three subclasses of glutamate receptors (i.e., the NMDA receptor) is sufficient to convey substantial neuronal resistance to both glutamate neurotoxicity and to hypoxic injury. However, it has further been determined that the indolactam compounds of the invention appeared to interact with all three subclasses of glutamate receptors, thereby providing a broader based neuronal resistance to glutamate neurotoxicity than was available for other compounds previously developed in the laboratories of the present inventors, such as the mirror-image enantiomers of the opioids.

On the other hand, the compounds of the invention do not appear to block kainate-induced whole-cell currents in corticoneurons and hence are probably not working by direct receptor antagonism. Presumably, these drugs act on other events that link receptor activation to neuronal degeneration. Lack of receptor-like activity is also in accordance with the finding that a specific stereochemistry is not required in order to provide protection of central neurons against toxic injury.

The method of the invention is carried out by administering to a patient susceptible to neurotoxic injury an amount of a compound of the invention sufficient to reduce neurotoxic effects on central neurons (brain, brain stem, spinal cord, or retinal). The method is suitable for use in any animal species having glutamate and other excitatory amino acid receptors. The term patient is intended to include any such animal to which a compound of the invention would be administered for the indicated purpose, including both medicinal and veterinary uses. Use in mammals and birds of all types is preferred, with use in humans being a primary utility.

Administration can be by any technique capable of introducing a compound of the invention into the bloodstream of the patient, including oral administration and intravenous, intramuscular, and subcutaneous injections, referred to collectively as parenteral injections. Preparation of organic compounds for administration to patients, particularly humans, is well known and can be applied directly to administration of the compounds of the present invention.

Typical doses in orally acceptable pharmaceutical carriers would be from 50 mg to 5 g, preferably from 100 mg to 1 g. These doses are for administration to a typical 70-kg human, and might be repeated several times per day to maintain brain extracellular levels at several micromolar. Administration can be adjusted to provide the same relative dose per unit of body weight. A preferred range for concentration of active compounds in contact with central neurons is from about 0.1 to about 20 micromolar.

A preferred formulation comprises a pharmacologically active compound of the invention and an inert carrier suitable for use as an injectable solution or suspension. Injectable compositions are preferred because of the likelihood that a patient suffering from neurotoxic injury will not be able to take compounds orally. Aqueous solutions, optionally containing minor amounts of an organic solvent, such as ethanol, for use in increasing solubility, are particularly preferred. Preferred is an injectable solution containing from 50 mg to 5 g, preferably from 100 mg to 1 g of the indolactam. The amount utilized for any particular patient will vary depending on the body weight and particular use, as is well understood in the art. Typical concentrations in the bloodstream on the order of 0.1-100 micromolar, preferably 1-20 micromolar, will be useful.

Injectable formulations of the invention will differ from simple aqueous solutions in that they have been formulated for pharmaceutical use and therefore will not contain pyrogens and other substances that may be present in typical laboratory solutions of organic compounds.

All compounds of the invention can be made by standard techniques that are available for producing indolactams. Total synthetic syntheses of indolactams have been reported. For example, see Nakatsuka et al., *Tetrahedron Lett.*, (1987) 28:2265-2268; Moritaki et al., *Tetrahedron Lett.*, (1988) 29:6267-6270; Okabe et al., *Chem. Pharm. Bull.*, (1989) 37:563-564. Additionally, compounds having the (−)-indolactam V ring system can be isolated from natural sources, as indicated by a number of references set forth in the background section of the specification. A number of indolactams are available commercially from chemical suppliers, such as LC Services Corp., Woburn, Mass. It is well known that synthetic procedures for synthesizing chiral compounds will give rise to both enantiomers (in the absence of special techniques, for example those involving reactants or catalysts that themselves are optically active). Enantiomers are generally resolved by forming a salt or other derivative of the enantiomers with an optically active compound. The resulting diastereomers have different physical properties and can be separated. Accordingly, compounds of the invention can be prepared utilizing the same techniques as those utilized to produce known indolactams with selection for use as preferred compounds of the enantiomer that is normally discarded when a phorbol-ester-like agonist or antagonist is being synthesized.

It is also possible to synthesize compounds of the invention without attention to separation of isomers or use of stereospecific techniques. Since enantiomers having opposite stereochemistry have been demonstrated to both have the desired activity, mixtures of isomers can be synthesized and used without separation of isomers. Since side effects such as phorbol-ester-like activity are generally more pronounced with just one of the isomers, the other isomer or isomers present add to the desired protective effect while diluting the side effect.

The following examples are provided for purposes of illustration only and are not to be considered limiting of the invention unless otherwise specified.

EXAMPLES

Mixed cortical cell cultures, containing both neuronal and glial elements, were prepared as previously described (Choi, D.W., *Neurosci. Lett.* (1985) 58:293-297 from fetal mice at 14-17 days gestation. Dissociated cortical cells were plated in 15-mm multiwells in Eagle's minimal essential medium (MEM—Earl's salts) supplemented with 10% heat-inactivated horse serum, 10% fetal bovine serum, glutamine (2 mM), and glucose (21 mM). Cultures were maintained at 37° C. in a humidified $CO_2$-containing atmosphere. After 5-12 days in vitro, non-neuronal cell division was halted by 1-3 days of exposure to $10^{-5}$M cytosine arabinoside, and the cells were shifted into a maintenance medium similar to the plating media, but lacking fetal serum. Subsequent media replacement was carried out on a biweekly schedule. Under these conditions, neurons (phase-bright when viewed under a phase-contrast microscope and bearing extensive processes) form an extensive, synaptically active network on top of an astrocyte (glial-fibrillary-acidic-protein-containing) monolayer.

Exposure to glutamate agonists (20–50 μM kainate, 10 μM AMPA, or 15 μM NMDA) was via the bathing medium, utilizing defined solutions lacking serum, glutamate, or lactate dehydrogenase. Care was taken to wash out the normal medium from cultures prior to addition of the excitatory amino acid exposure solutions. Exposures were carried out for 24 to 48 hours in the culture incubator, using a defined medium consisting of Eagle's minimal essential medium (Earle's salts) supplemented only with glucose (total 25 mM). In control experiments, this simplified culture medium was well tolerated by cortical cell cultures for several days.

Quantitative assessment of neuronal injury was accomplished by measuring the extracellular concentration of the cytosolic enzyme lactate dehydrogenase (LDH) released to the culture medium by damaged neurons. Control experiments showed that the spontaneous release of LDH was low, that the appearance of extracellular LDH correlated well with morphological evidence of neuronal injury, and that no LDH was released when glia alone were exposed to 0.5 mM glutamate for 5 minutes.

LDH was measured immediately following excitatory amino acid exposure in the culture medium at room temperature using the method of Wroblewski and LaDue (Wroblewski, F. and LaDue, J.S., *Proc. Soc. Exp. Biol. Med.* (1955) 90:210–213). Samples of media (0.1 ml) were added to 2.3 moles of Na pyruvate and 0.2 mg of added NADH in 0.1 M $KPO_4$ buffer (pH 7.5 at 25°) (total volume 3 ml). The absorbance of the reaction mixture at 340 nm, an index of NADH concentration, was measured with a spectrophotometer at 2 second intervals; LDH concentration was then calculated from the slope of the absorbance curve, fit by linear regression to the linear (initial) portion of the curve, and corrected for temperature and light path. Accuracy of the assay was verified by periodic checks of a standard LDH enzyme solution (Sigma Enzyme Control 2-E).

Exposure of cortical cell cultures to excitatory amino acids alone resulted in disintegration of substantial numbers of neurons; many remaining neurons failed to exclude trypan blue dye. LDH measurements showed a substantial rise (typically 30–70% of maximal neuronal LDH) in extracellular enzyme compared with the background appearance of LDH in cultures not exposed to excitatory amino acids.

On the other hand, when compounds of the invention were added to the excitatory amino acid exposure solution, both the morphological and the chemical evidence of neurotoxicity was markedly attenuated. Four compounds specifically tested were (−)-indolactam V, (+)-indolactam V, (−)-7-octylindolactam V, and (+)-7-octylindolactam V. Concentrations in the range of from 0.1 to 30 μM were tested.

Specifically, these compounds blocked from 50% to 80% of the neuronal loss induced by 24- to 48-hr exposure of test cells as described above to kainate, AMPA, or NMDA. The most active of these four compounds was the (+)-7-octylindolactam V.

The present results indicate that indolactams can substantially reduce the vulnerability of cortical neurons in mixed cell cultures to damage by exposure to several different glutamate receptor agonists. The test procedure described above can be used with indolactams having unknown biological activity to determine such activity relative to known compounds, such as those described in these examples.

All publications (including patents) and patent applications cited in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended

What is claimed is:

1. A method for reducing adverse effects of neurotoxic injury, which comprises:
   administering to a patient susceptible to neurotoxic injury an amount sufficient to reduce said effects of a compound having an indolactam V ring system of the formula

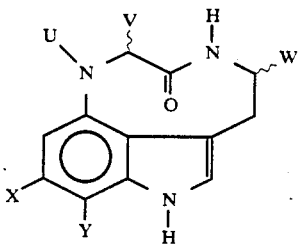

wherein:

U is H or methyl;

V is H or an alkyl group of 1 to 5 carbon atoms;

W is H, an alkyl group of 1 to 5 carbon atoms, or an alkyl group of 1 to 5 carbon atoms substituted with a hydroxyl group; and X and Y independently represent hydrogen or a hydrocarbon substituent containing up to 15 carbon atoms.

2. The method of claim 1, wherein X or Y is a hydrocarbon substituent.

3. The method of claim 2, wherein X represents hydrogen.

4. The method of claim 1, wherein Y represents a hydrocarbon group.

5. The method of claim 4, wherein Y represents a linear alkyl group.

6. The method of claim 5, wherein Y represents an octyl group.

7. The method of claim 2, wherein Y represents an isoprenoid.

8. The method of claim 2, wherein X and Y when taken together with ring carbons at positions 6 and 7 represent a cyclic hydrocarbon group having 6-ring members.

9. The method of claim 1, wherein U is a methyl group.

10. The method of claim 1, wherein V is an isopropyl group.

11. The method of claim 1, wherein W is a hydroxymethyl group.

12. The method of claim 1, wherein said neurotoxic injury involves neurons in the brain, brain stem, spinal cord, or retina.

13. The method of claim 1, wherein said amount is sufficient to provide a concentration of from about 0.1 to about 20 micromolar at a central neuron subject to said neurotoxic injury.

14. The method of claim 1, wherein said administering is by oral ingestion or parenteral administration.

15. The method of claim 14, wherein said amount is by parenteral administration in a single dose to a human and is from about 50 mg to about 5 g.

16. The method of claim 14, wherein said amount is by continuous parenteral infusion and is from about 1 to about 300 mg/kg/day.

17. The method of claim 1, wherein said compound is (+)-7-octylindolactam V, said administering is by parenteral injection, and said amount is from about 1 to about 300 mg/kg/day either as divided doses or as a continuous infusion.

18. The method according to claim 1 wherein:
U is a methyl group,
V is an isopropyl group,
W is a hydroxymethyl group,
X is hydrogen and
Y is n-octyl group.

* * * * *